(12) United States Patent
Ranucci et al.

(10) Patent No.: US 12,161,334 B2
(45) Date of Patent: *Dec. 10, 2024

(54) SURGICAL INSTRUMENT WITH AN ACTUATION LOCKOUT

(71) Applicant: C.R. Bard, Inc., Murray Hill, NJ (US)

(72) Inventors: Kevin J. Ranucci, Warwick, RI (US); Nathan Stewart Cauldwell, Hope, RI (US); Augustus Felix, Cranston, RI (US)

(73) Assignee: C.R. Bard, Inc., Murray Hill, NJ (US)

( * ) Notice: Subject to any disclaimer, the term of this patent is extended or adjusted under 35 U.S.C. 154(b) by 102 days.

This patent is subject to a terminal disclaimer.

(21) Appl. No.: 17/876,037

(22) Filed: Jul. 28, 2022

(65) Prior Publication Data

US 2022/0361878 A1 Nov. 17, 2022

Related U.S. Application Data

(60) Continuation of application No. 16/845,202, filed on Apr. 10, 2020, now Pat. No. 11,457,919, which is a (Continued)

(51) Int. Cl.
*A61B 17/10* (2006.01)
*A61B 17/068* (2006.01)
(Continued)

(52) U.S. Cl.
CPC ............ *A61B 17/10* (2013.01); *A61B 17/068* (2013.01); *A61F 2/0063* (2013.01);
(Continued)

(58) Field of Classification Search
CPC .................. A61B 17/10; A61B 17/068; A61B 2017/00309; A61B 2017/0647;
(Continued)

(56) References Cited

U.S. PATENT DOCUMENTS 5,470,007 A 11/1995 Plyley et al.
5,554,169 A 9/1996 Green et al.
(Continued)

FOREIGN PATENT DOCUMENTS

EP 0 399 701 A1 11/1990
EP 1 479 347 A1 11/2004
(Continued)

*Primary Examiner* — Tuan V Nguyen
(74) *Attorney, Agent, or Firm* — Wolf, Greenfield & Sacks, P.C.

(57) ABSTRACT

Embodiments of a surgical instrument and its methods of use are disclosed. The disclosed embodiments of a surgical instrument may include a handle and an elongated shaft assembly distally extending from the handle. The elongated shaft assembly may include an articulable portion. An articulation control may be associated with the elongated shaft assembly. The articulation control may be movable between a first position in which the elongated shaft assembly is arranged in a first articulation position and a second position in which the elongated shaft assembly is arranged in a second articulation position. The surgical instrument may include a fastener deployment system with a locking member. The articulation control may block movement of the locking member when the articulation control is located in the first position. The articulation control may also permit movement of the locking member when the articulation control is located in the second position.

25 Claims, 4 Drawing Sheets

Related U.S. Application Data continuation of application No. 15/485,707, filed on Apr. 12, 2017, now Pat. No. 10,653,419, which is a division of application No. 13/826,808, filed on Mar. 14, 2013, now Pat. No. 9,649,109.

(51) Int. Cl.
*A61F 2/00* (2006.01)
*A61B 17/00* (2006.01)
*A61B 17/064* (2006.01)
*A61B 17/29* (2006.01)

(52) U.S. Cl.
CPC ............... *A61B 2017/00309* (2013.01); *A61B 2017/0647* (2013.01); *A61B 2017/2929* (2013.01); *A61F 2002/0072* (2013.01)

(58) Field of Classification Search
CPC ..... A61B 2017/2929; A61B 2017/0072; A61F 2/0063
See application file for complete search history.

(56) References Cited

U.S. PATENT DOCUMENTS

| | | | |
|---|---|---|---|
| 5,665,105 A | | 9/1997 | Furnish et al. |
| 5,766,196 A | * | 6/1998 | Griffiths .............. A61B 17/29 606/174 |
| 5,823,066 A | | 10/1998 | Huitema et al. |
| 5,827,263 A | | 10/1998 | Furnish et al. |
| 5,792,165 A | | 11/1998 | Klieman et al. |
| 6,042,601 A | | 3/2000 | Smith |
| 6,821,282 B2 | | 11/2004 | Perry et al. |
| 7,559,930 B2 | | 7/2009 | Allard et al. |
| 7,771,440 B2 | | 8/2010 | Ortiz et al. |
| 7,780,055 B2 | | 8/2010 | Scirica et al. |
| 7,819,296 B2 | | 10/2010 | Hueil et al. |
| 7,832,612 B2 | | 11/2010 | Baxter et al. |
| 7,866,527 B2 | | 1/2011 | Hall et al. |
| 7,886,953 B2 | | 2/2011 | Schwemberger et al. |
| 7,931,660 B2 | | 4/2011 | Aranyi et al. |
| 8,105,350 B2 | | 1/2012 | Lee et al. |
| 8,795,325 B2 | | 8/2014 | Taylor et al. |
| 9,649,109 B2 | | 5/2017 | Ranucci et al. |
| 10,653,419 B2 | | 5/2020 | Ranucci et al. |
| 11,457,919 B2 | | 10/2022 | Ranucci et al. |
| 2004/0232199 A1 | | 11/2004 | Shelton, IV et al. |
| 2008/0061108 A1 | | 3/2008 | Scirica |
| 2008/0173689 A1 | | 7/2008 | Spasov et al. |
| 2008/0314958 A1 | | 12/2008 | Scirica |
| 2009/0206132 A1 | | 8/2009 | Hueil et al. |
| 2009/0236395 A1 | | 9/2009 | Scirica |
| 2009/0312603 A1 | | 12/2009 | Lam et al. |
| 2012/0199629 A1 | | 8/2012 | Cappola et al. |
| 2014/0263544 A1 | | 9/2014 | Ranucci et al. |
| 2017/0215882 A1 | | 8/2017 | Ranucci et al. |
| 2020/0237373 A1 | | 4/2020 | Ranucci et al. |

FOREIGN PATENT DOCUMENTS

| | | |
|---|---|---|
| EP | 2 484 290 A1 | 8/2012 |
| JP | 2009-189824 A | 8/2009 |
| WO | WO 2012/125635 A2 | 9/2012 |
| WO | WO 2014/158523 | 2/2014 |

* cited by examiner

SURGICAL INSTRUMENT WITH AN ACTUATION LOCKOUT

CROSS-REFERENCE TO RELATED APPLICATIONS

This Application is a continuation of U.S. patent application Ser. No. 16/845,202, filed on Apr. 10, 2020, which is a continuation of U.S. patent application Ser. No. 15/485,707, filed on Apr. 12, 2017, which is a divisional application of U.S. patent application Ser. No. 13/826,808, filed on Mar. 14, 2013, the disclosures of each of which are incorporated herein by reference in its entirety.

FIELD

A surgical instrument with an actuation lockout.

BACKGROUND

A surgical mesh fabric or other prosthetic repair fabric may be used to surgically repair a hernia. The prosthetic repair fabric is typically implanted during an open procedure or laparoscopically. To secure the repair fabric in place, one or more fasteners may be deployed through the prosthetic repair fabric and into the underlying tissue. Some surgical instruments include an articulable portion to aid in deploying the fasteners at the surgical site.

SUMMARY

In one embodiment, a surgical instrument includes a handle and an elongated shaft assembly extending distally from the handle. The elongated shaft assembly includes an articulable portion. An articulation control is associated with the elongated shaft assembly. The articulation control is movable between a first position in which the elongated shaft assembly is arranged in a first articulation position and a second position in which the elongated shaft assembly is arranged in a second articulation position. The surgical instrument also includes a fastener deployment system including a locking member. The articulation control blocks movement of the locking member when the articulation control is located in the first position, and the articulation control permits movement of the locking member when the articulation control is located in the second position.

In another embodiment, a surgical instrument includes a handle and an elongated shaft assembly extending distally from the handle. The elongated shaft assembly includes an articulable portion. An articulation control is associated with the elongated shaft assembly. The articulation control is movable between a first position in which the elongated shaft assembly is arranged in a first articulation position and a second position in which the elongated shaft assembly is arranged in a second articulation position. The articulation control includes a blocking portion. The surgical instrument also includes a fastener deployment system including a locking member. The blocking portion of the articulation control is aligned with the locking member when the articulation control is located in the first position. Further, the blocking portion of the articulation control is not aligned with the locking member when the articulation control is located in the second position.

In yet another embodiment, a method for operating a surgical instrument includes: providing a surgical instrument including: a handle; an elongated shaft assembly extending distally from the handle, wherein the elongated shaft assembly includes an articulable portion; an articulation control associated with the elongated shaft assembly, wherein the articulation control is movable between a first position in which the elongated shaft assembly is arranged in a first articulation position and a second position in which the elongated shaft assembly is arranged in a second articulation position, wherein the articulation control includes a blocking portion; a fastener deployment system including a locking member; moving the articulation control to the unarticulated position to align the blocking portion with the locking member; and moving the articulation control to the articulated position to move the blocking portion out of alignment with the locking member.

It should be appreciated that the foregoing concepts, and additional concepts discussed below, may be arranged in any suitable combination, as the present disclosure is not limited in this respect. Further, the foregoing and other aspects, embodiments, and features of the present teachings can be more fully understood from the following description in conjunction with the accompanying drawings.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

Figure 1:
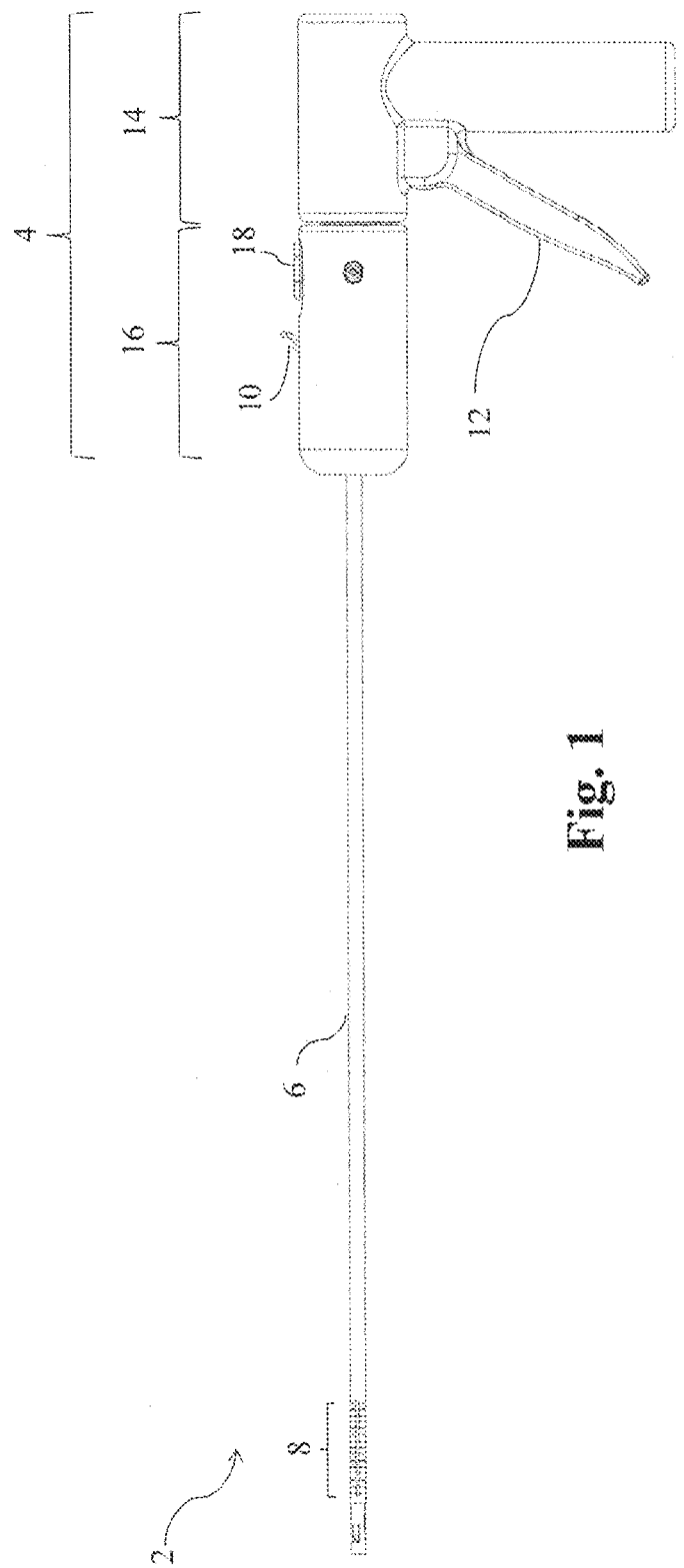
FIG. 1 is a schematic representation of a laparoscopic surgical instrument including an actuation lockout mechanism.

The inventors have recognized that it may be undesirable to deploy a fastener while the surgical instrument is located in the unarticulated position. Consequently, the inventors have recognized the need for an actuation lockout mechanism that prevents the deployment of a fastener depending on the articulation angle of the surgical instrument. Further, the inventors have recognized the benefits associated with incorporating at least a portion of an actuation lockout mechanism with the articulation control of the surgical instrument.

In one embodiment, the articulation control may selectively permit the actuation of the fastener deployment system of a surgical instrument by interacting with a locking member associated with, or included in, the fastener deployment system. Movement of the locking member is required to permit actuation of the fastener deployment system while blocking movement of the locking member prevents actuation of the fastener deployment system.

In addition to selectively blocking movement of the locking member, the articulation control is adjustable between one or more positions to articulate an elongated shaft assembly of the surgical instrument. Depending on the embodiment, the one or more positions may correspond to any number of preselected articulated positions such as an unarticulated position, a partially articulated position, and a fully articulated position. Alternatively, the articulation control, and correspondingly the elongated shaft assembly, may be arranged in any position between the fully articulated and unarticulated positions. Regardless of how many orientations the elongated shaft assembly may be articulated to, when the elongated shaft assembly is unarticulated, the articulation control will block movement of the locking member to prevent actuation of the fastener deployment system. Further, when the elongated shaft assembly is articulated to a preselected articulated position, or when the articulation angle of the elongated shaft assembly is greater than a preselected articulation angle, the articulation control may permit movement of the locking member to permit actuation of the fastener deployment system. Consequently, as described in more detail below, the articulation control may be positioned to selectively permit, or prevent, the actuation of the fastener deployment system.

In some embodiments, the articulation control may selectively permit movement of the locking mechanism through the use of a blocking portion and a non-blocking portion. For example, when the articulation control is located in the unarticulated position, the blocking portion of the articulation control may physically interfere with movement of the locking member. The blocking portion of the articulation control may be embodied by any number of different features including: an external surface of the articulation control; an extension or protrusion from the articulation control; or any other appropriate structure associated with the articulation control and capable of blocking movement of the locking member. Correspondingly, the non-blocking portion of the articulation control may be embodied by any number of different features including, but not limited to, through holes, blind holes, channels, cutouts, grooves, or any other appropriate structure associated with the articulation control that is sized and shaped to accommodate movement of the locking member. In addition, in some embodiments, the non-blocking portion might be deformable such that movement of the locking member compresses the non-blocking portion of the articulation control. In other alternative embodiments, instead of having a non-blocking portion that is constructed and arranged to accommodate movement of the locking member, the articulation control may be constructed and arranged to be moved out of the way to permit movement of the locking member. For example, the articulation control may block movement of the locking member in the unarticulated position and the articulation control may be moved out of the path of the locking member when it is positioned in the articulated position to permit movement of the locking member.

As noted above, the locking member may be associated with, or incorporated into, the fastener deployment system of the surgical instrument. Further, the locking member may be associated with any appropriate component of the fastener deployment system such that blocking movement of the locking member prevents actuation of the fastener deployment system. For example, the locking member may be associated with a drive shaft, a power assist, a full power mechanism, a gear transmission, a linkage transmission, a trigger, or any other appropriate component of the fastener deployment system. Further, the locking member may be sized, shaped, and arranged to interact with the blocking and non-blocking portions of the articulation control as detailed above. For example, the locking mechanism might be embodied as a rod, a crossbar, an extension, or a projection associated with a component of the fastener deployment system. In some embodiments, the locking member may have a size and shape that complements the non-blocking portion of the articulation control (e.g. a rod sized and shaped to fit in a through hole). Alternatively, the locking member may have a dissimilar size and shape as the non-blocking portion of the articulation control. In either case, the locking member may be adapted to be movable when aligned with the non-blocking portion of the articulation control. In addition, the locking member may be assembled, or integrally formed, with any appropriate component of the fastener deployment system as the current disclosure is not limited in this manner.

In a representative procedure, a surgical instrument incorporating an actuation lockout mechanism, as described above, and arranged in the unarticulated position, is inserted into a surgical field. As the surgical instrument is inserted in the unarticulated position, the fastener deployment system of the surgical instrument is prevented from firing due to the interaction of the locking member and the articulation control. A practitioner may articulate the tip of the surgical instrument and then position the articulated tip at the surgical site. With the surgical instrument articulated, the articulation control is arranged to permit movement of the locking member and enables the fastener deployment system to deploy a fastener. After deploying one or more fasteners, the surgical instrument may be unarticulated and removed from the surgical field.

While specific embodiments of the articulation control and the locking mechanism are described herein, it should be understood that any number of constructions and arrangements are possible for both the articulation control as well as the locking mechanism. Therefore, other embodiments including different constructions and arrangements of the articulation control and the locking mechanism are also envisioned.

For the sake of clarity, the currently disclosed embodiments are directed to a laparoscopic device for use in deploying one or more fasteners. However, the current disclosure is not limited to laparoscopic devices for use in deploying one or more fasteners. Instead, the actuation lockout mechanisms could be used in any surgical instrument including an articulating tip and an end effector system. For example, an actuation lockout mechanism could be incorporated into an endoscopic device, a borescopic device, a catheter, a surgical instrument for use in "open" procedures, or any other appropriate surgical instrument. Additionally, in some embodiments, the instrument including the actuation lockout mechanism might be loaded with one or more fasteners, or it may be constructed to allow the user to load the instrument with one or more fasteners. Further, the disclosed embodiments related to deploying a fastener are described with regards to a generic fastener. Consequently, any appropriate fastener could be used with the currently disclosed actuation lockout mechanism including a tack, a clip, a staple, a pin, a tissue anchor, a bone anchor, or any other appropriate type of fastener.

Turning now to the figures, specific embodiments of an actuation lockout mechanism are described.

FIG. 1 presents one embodiment of a surgical instrument 2. The surgical instrument includes a handle 4 and an elongated shaft assembly 6 extending distally from the handle 4. In addition to fasteners being deployed from a distal end of the elongated shaft assembly 6, the elongated shaft assembly may also include an articulable portion 8. Articulation of the articulable portion 8 may be controlled by articulation control 10 which may be moved between one or more positions to articulate the articulable portion 8 to a desired articulation angle. Surgical instrument 2 may also include a trigger 12 for actuation of a fastener deployment system 102, see FIG. 3. It should be noted that while a particular arrangement of components corresponding to the surgical instrument 2 has been described, other arrangements of the depicted components as well as other possible components might be used as the current disclosure is not limited in this fashion.

The articulable portion 8 may be articulated between an unarticulated (i.e. straight) position and a fully articulated position. In some embodiments, the articulable portion 8 may be articulated to only the unarticulated position and the fully articulated position. In other embodiments, the articulable portion 8 may be articulated to one or more preselected articulated positions, or any position between the unarticulated position and the fully articulated position as the current disclosure is not limited in this fashion. Further, depending upon the embodiment, the articulable portion 8 may only be articulated in one direction, or it may be articulated in two directions. For example, the articulable portion 8 may be articulated between articulation angles of approximately 0° and 90°, 0° and 45°, −90° and 90°, −180° and 180°, or any appropriate range of angles. Further, in some embodiments, the articulable portion 8 may be articulated about two or more axes (e.g. articulation in the horizontal and vertical directions). However, regardless of the specific directions and ranges of motion, articulation of the articulable portion 8 may be provided by any appropriate articulation mechanism. For example, the articulable portion 8 might be articulated using: one or more control wires, ribbons, or slats associated with the articulable portion 8; two or more coaxial tubular members with displaced neutral bending axes; prestressed tubular members and retractable alignment sheaths; rigid articulation linkages; or any other appropriate structure capable of articulating articulable portion 8.

Figure 2:
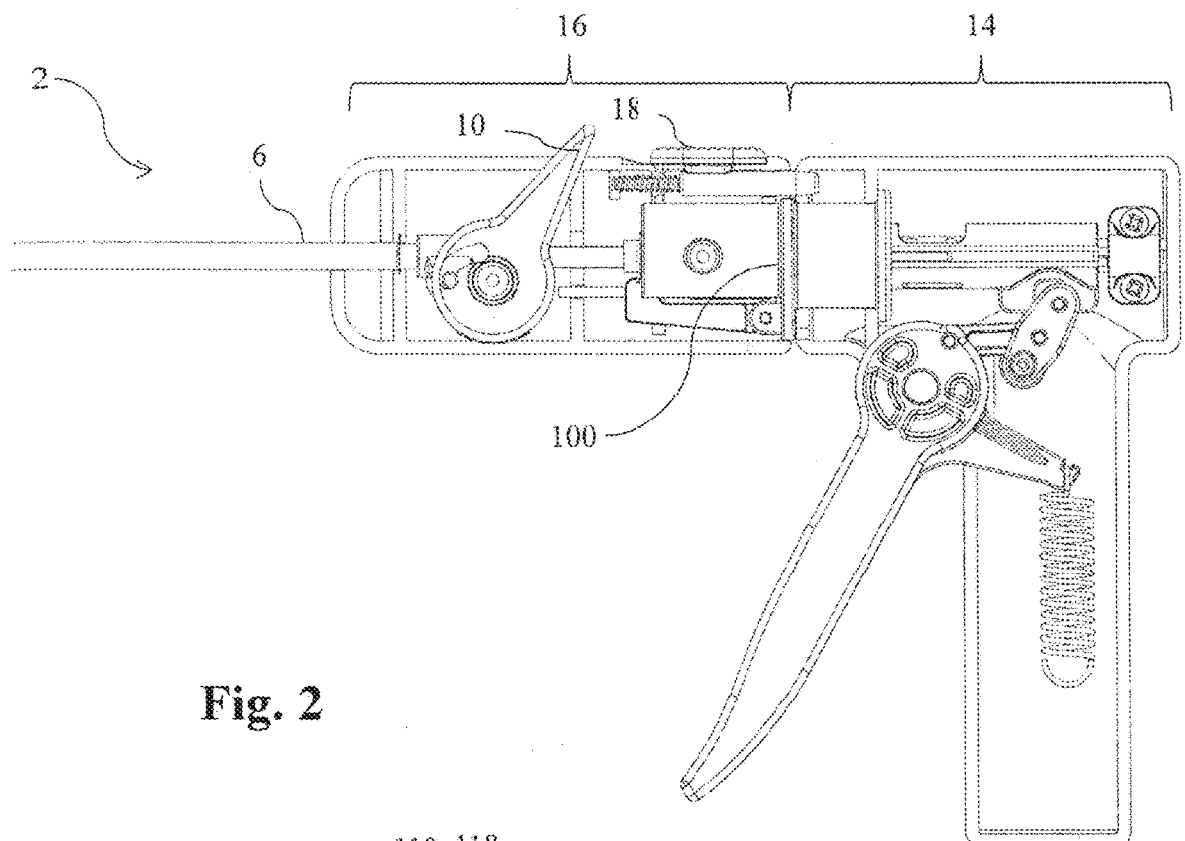
FIG. 2 is a schematic representation of the surgical instrument of FIG. 1 with one half of the outer shell removed.

In addition to articulation, in some embodiments, it may be desirable to rotate the elongated shaft assembly 6 to facilitate positioning of the distal tip. This rotation of the elongated shaft assembly 6 may be provided in any appropriate manner. For example, the elongated shaft assembly 6 may simply be adapted to be rotatable to at least a portion of the handle 4. Alternatively, a portion of the handle 4 including the elongated shaft assembly 6 may be rotatable relative to a portion of the handle 4 including the grip. One such embodiment is depicted in FIG. 1. In the depicted embodiment, the surgical instrument 2 includes a first handle portion 14 and a second handle portion 16 including the elongated shaft assembly 6. The first and second handle portions 14 and 16 may be constructed and arranged in any appropriate fashion to be rotatable relative to one another. The handle 4 may also include a rotational housing 100, see FIG. 2, for rotatably coupling the first handle portion 14 and the second handle portion 16. The rotational housing may be fixed in a preselected orientation relative to the first handle portion. However, embodiments in which the rotational housing 100 is free to rotate with respect to the first handle portion 16 are also envisioned. The first and second handle portions 14 and 16 may be locked in a particular orientation through the use of any appropriate handle rotation locking mechanism 18. While a spring biased locking mechanism is depicted in the figures any appropriate locking mechanism might be used. For example, detents, frictional locks, or latches might be used to provide selective rotational locking of the separate handle portions. In addition, while a surgical instrument including rotatable portions and/or a rotatable elongated shaft assembly is described above, surgical instruments including a unitary handle and/or an elongated shaft assembly that is stationary relative to the handle are also envisioned.

Figure 3:
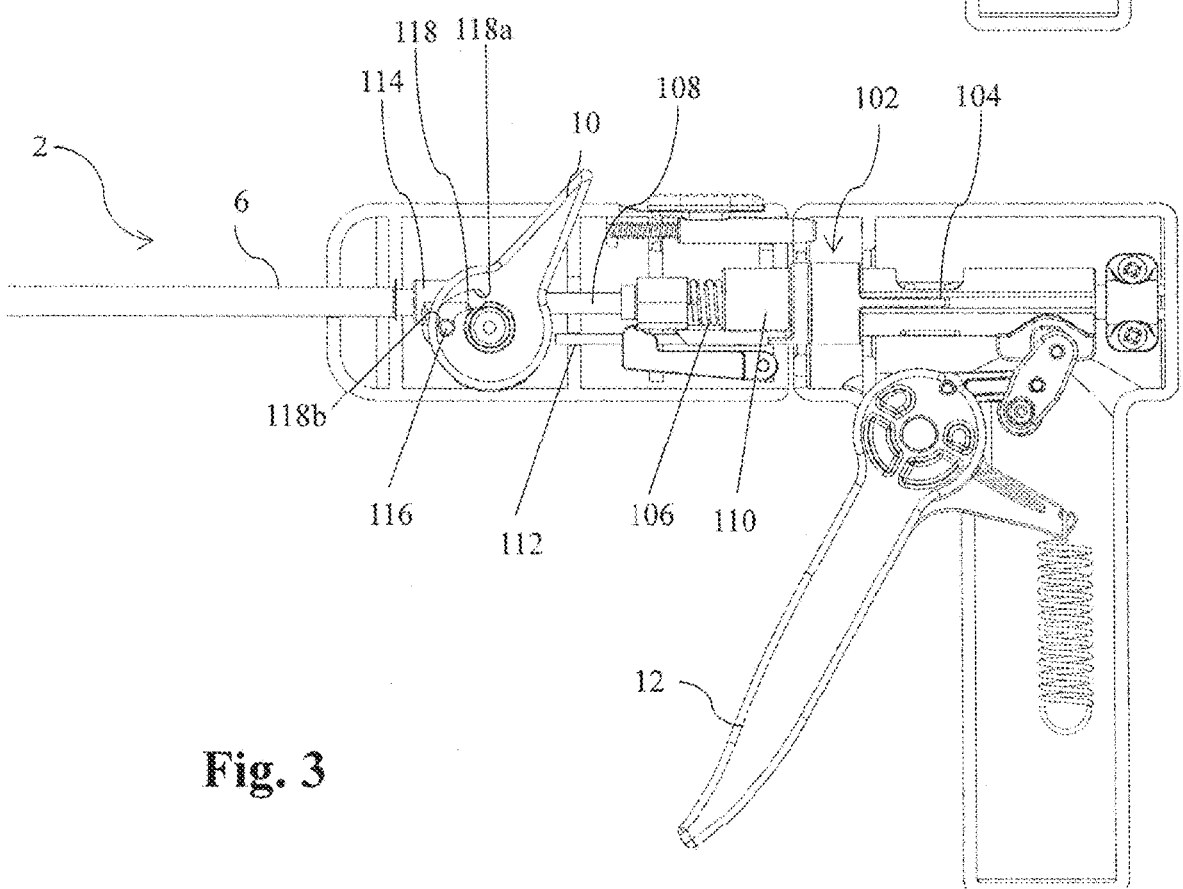
FIG. 3 is a schematic representation of the surgical instrument of FIG. 2 with the rotational coupling removed for visualization purposes.

FIG. 3 depicts one embodiment of the interior components of the surgical instrument 2 with the rotational housing 100 removed for clarity and visualization of the fastener deployment system 102. As noted above, the fastener deployment system 102 may be embodied in any number of different ways. However, in the particular embodiment depicted in the figure, the fastener deployment system 102 includes a trigger 12, a shuttle 104, a power assist device 106, a driveshaft 108, a power assist housing 110, and a locking member 112 as well as other components that are not depicted. Actuation of the trigger 12 distally displaces the shuttle 104 to store energy in the power assist device 106 and/or displace the driveshaft 108. After a preselected amount of actuation, the power assist device 106 releases the stored energy to distally accelerate the driveshaft 108 and deploy a surgical fastener from the distal end of the elongated shaft assembly 6. The depicted power assist device 106 may correspond to any appropriate mechanism capable of aiding in deploying a fastener from the elongated shaft assembly 6 of the surgical instrument. In one specific embodiment, the power assist device 106 corresponds to the power assist device disclosed in U.S. patent application Ser. No. 13/804,043 entitled POWER ASSIST DEVICE FOR A SURGICAL INSTRUMENT filed on the same day as the current application.

Depending on the particular embodiment, the power assist device 106 may supply all of the power necessary to deploy a fastener, or it may only supply a portion of the power necessary to deploy a fastener. It should also be understood that any appropriate power assist device might be used, as the current disclosure is not limited to being used with any particular power assist device. Further, while a surgical instrument including a power assist device has been depicted, in some embodiments, the surgical instrument 2 may not include a power assist device, in which case actuation of the trigger 12 might directly displace driveshaft 108 to deploy a fastener from a distal end of the elongated shaft assembly 6.

In the embodiment depicted in FIG. 3, the articulation control 10 is a rotatable component that includes a slot 118. The slot 118 is sized and shaped to interact with a corresponding pin 116 extending outward from an associated articulation coupling 114. When the articulation control 10 is rotated, the pin 116 may be moved in either a proximal or distal direction to displace the articulation coupling 114 and articulate, or straighten, the articulable portion 8. In one embodiment, movement of the articulation coupling 114 may bias inner and outer tubular members with offset neutral axes to articulate the articulable portion 8. The depicted slot 118 may be shaped to provide two positions for the pin 116 to define the unarticulated position and the fully articulated position of articulable portion 8. The two positions are defined by surfaces 118a and 118b of the slot 118. Further, in some embodiments, the slot 118 may be shaped and arranged to include more than two resting positions to provide a plurality of articulated positions. Alternatively, the slot 118 may provide a gradual transition between the unarticulated and fully articulated position. In such an embodiment, the articulation control 10 might be retained, or locked, at any position between the unarticulated and fully articulated position to provide a continuum of possible articulation angles. As noted above, in some embodiments, it may be desirable to provide articulation in two directions (i.e. up and down). In such an embodiment, the slot 118 may be shaped and arranged to include a first resting position corresponding to the unarticulated position as well as one or more resting positions on either side of that first resting position to enable articulation of the articulable portion 8 in both directions.

Figure 4:
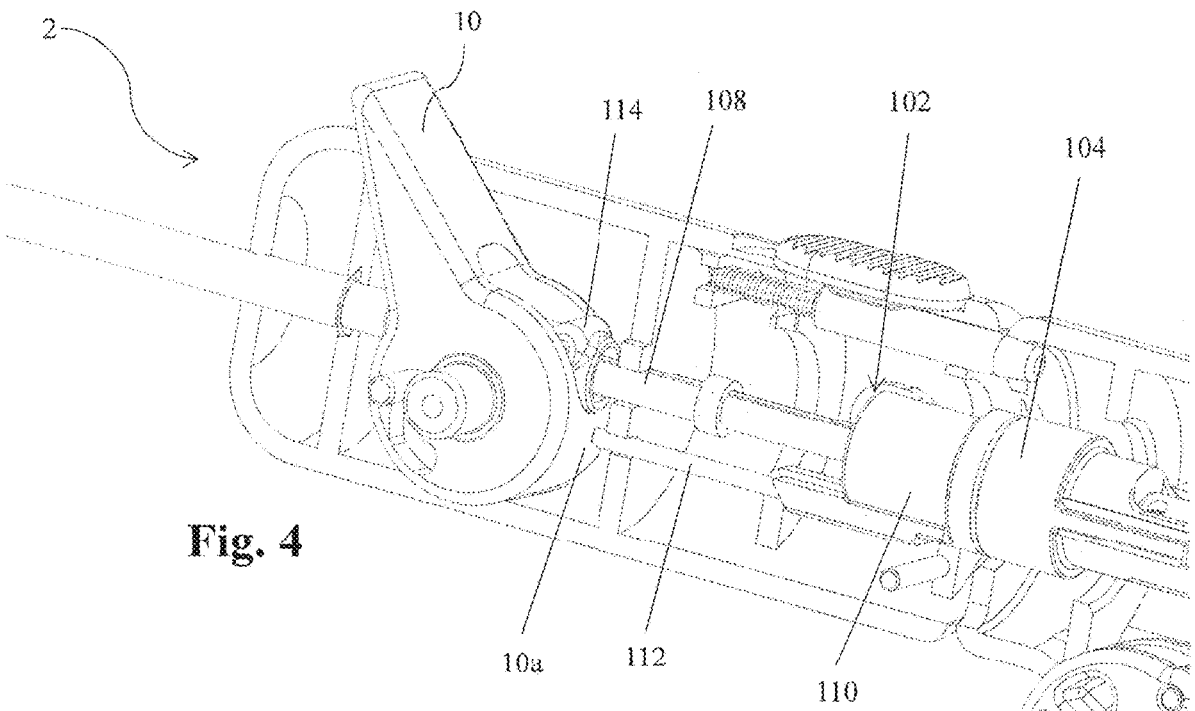
FIG. 4 is a schematic representation of a surgical instrument with the articulation control in the unarticulated position and the actuation mechanism blocked from actuating.
Figure 5:
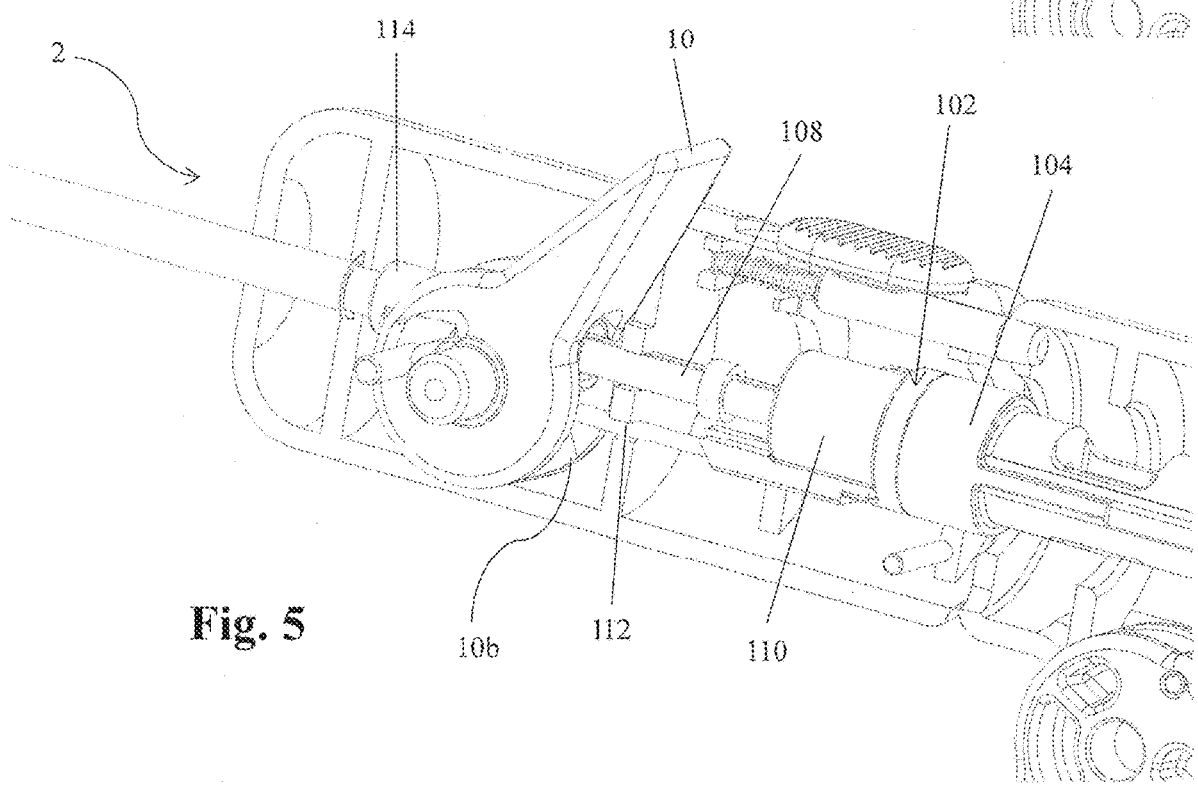
FIG. 5 is a schematic representation of a surgical instrument with the articulation control in the articulated position and the actuation mechanism in the actuated position.

For the sake of clarity, in FIGS. 4 and 5 portions of the power assist device have been removed to better illustrate movement of various components of the fastener deployment system 102 and the locking member 112 relative to the articulation control 10 during actuation of the surgical instrument.

FIG. 4 depicts one embodiment of the surgical instrument 2 with the articulation control 10 located in the unarticulated position and the fastener deployment system 102 prevented from actuating. As illustrated by the figure, while the articulation control 10 is positioned in the unarticulated position, the locking member 112 is aligned with and blocked from moving distally by a blocking portion 10a of the articulation control 10. Blocking movement of the locking member 112 interferes with movement of one or more features of the fastener deployment system required for operation of the fastener deployment system. For example, in the depicted embodiment, the locking member 112 is associated with the power assist housing 110. Thus, blocking the distal movement of the locking member 112 also prevents the distal movement of the power assist housing 110. Consequently, the fastener deployment system 102 is prevented from actuating while the articulation control 10 is in the unarticulated position. It should be understood that while the locking member 112 is associated with power assist housing 110 in the depicted embodiment, the locking member 112 could be associated with any appropriate component of the fastener deployment system including, but not limited to, the shuttle 104, another component of the power assist device 102, the driveshaft 108, or the trigger 12. Additionally, while the locking member 112 has been depicted as a distally extending rod and the blocking portion 10a has been depicted as an external surface of the articulation control 10, other constructions and arrangements of the locking member and blocking portion are also envisioned.

When desired, a user may reposition the articulation control 10 from, for example, the first unarticulated position to a second articulated position corresponding to a desired articulation angle of the articulable portion 8, see FIG. 5. In the depicted embodiment, once the articulation control 10 is moved from the unarticulated position past a preselected threshold corresponding to a preselected articulation angle, a non-blocking portion 10b of the articulation control is brought into alignment with the locking member 112. The depicted non-blocking portion 10b is a cutout or relief formed in the articulation control 10 and it is sized and shaped to accommodate distal movement of the locking member 112. However, other arrangements and features corresponding to the non-blocking portion 10b are also envisioned. However, regardless of the specific feature corresponding to the non-blocking portion 10b, when the non-blocking portion 10b is aligned with the locking member 112, the non-blocking portion 10b is adapted and arranged to accommodate distal movement of the locking member 112 throughout an actuation cycle of the fastener deployment system 102. Consequently, upon actuation of the trigger, the shuttle 104, the power assist housing 110, and the driveshaft 108 may be actuated to deploy a fastener from the surgical instrument.

While the articulation control 10 has been depicted as being rotated to align the blocking portion 10a and the non-blocking portion 10b of the articulation control with the locking member 112 to selectively permit or block actuation of the fastener deployment system, other movements of the articulation control are also contemplated. For example, the articulation control may be rotated or linearly displaced in any appropriate direction to align the blocking portion and non-blocking portion of the articulation control with the locking member. In addition, in some instances, the articulation control may be displaced in a combination of directions. However, regardless of the specific direction, or method, of displacing the articulation control, displacement of the articulation control between an unarticulated position and an articulated position may selectively align the blocking portion and non-blocking portion of the articulation control with the locking member to selectively permit, or prevent, actuation of the fastener deployment system.

Figure 6:
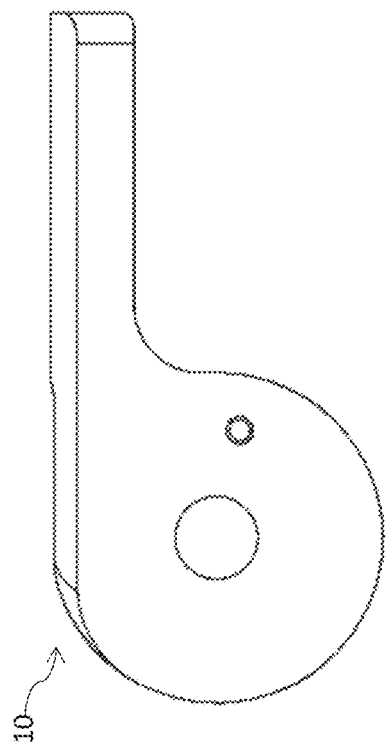
FIG. 6 is a schematic side view of an articulation control including through holes for actuation lockout.
Figure 7:
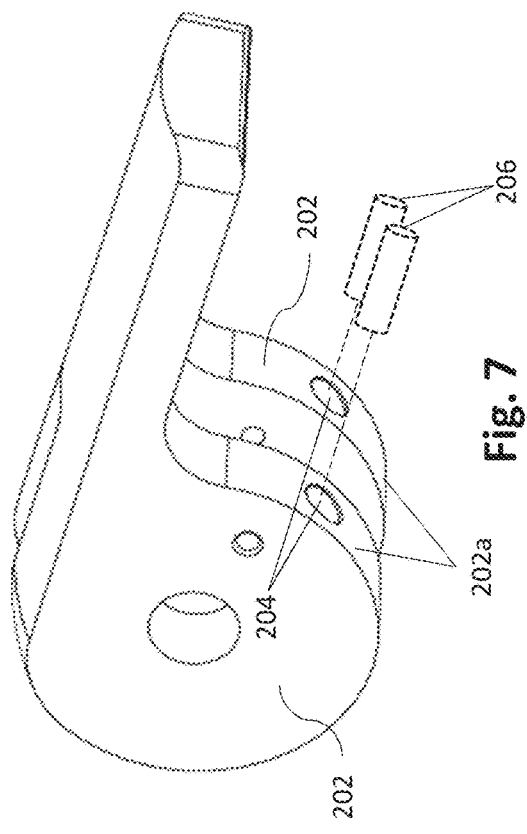
FIG. 7 is a schematic perspective view of the articulation control of FIG. 6.
Figure 8:
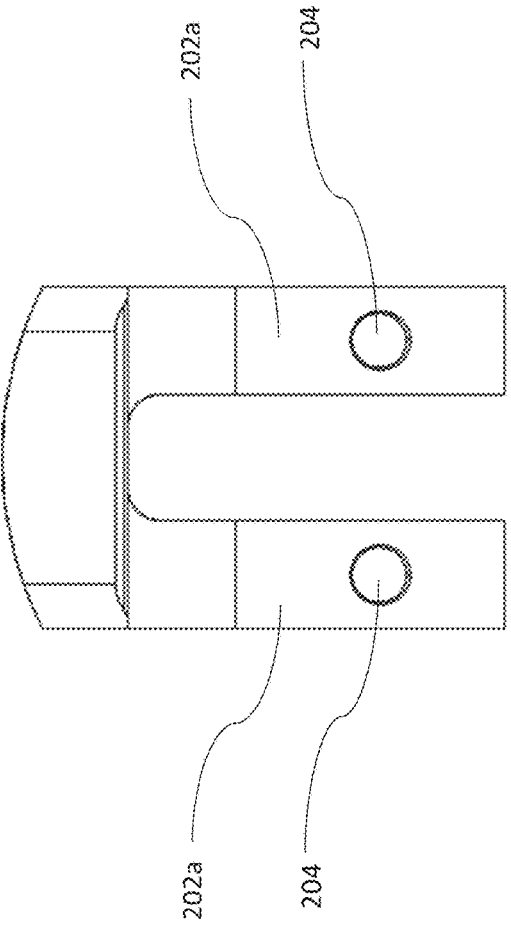
FIG. 8 is a schematic rear view of the articulation control of FIG. 6.

In some embodiments, it may be desirable to have more than one locking member and/or more than one associated blocking and non-blocking portions of the articulation control (i.e. a plurality of locking members and a plurality of associated blocking and non-blocking portions). Such an embodiment might desirably provide a redundancy for the actuation lockout mechanism in case a single portion of the actuation lockout mechanism were non-functional. FIGS. 6-8 depict an embodiment of the articulation control 10 including two blocking and two non-blocking portions. In the depicted embodiment, the articulation control 10 is rotatable and includes two supports 202 separated by a central channel. The central channel is sized and shaped to accommodate a distally extending driveshaft disposed between the supports 202. Additionally, the supports 202 include external surfaces 202a that may act as the two blocking portions of the actuation control. The supports 202 also include through holes 204 that may act as the non-blocking portions of the actuation control when aligned with corresponding locking members 206 that are sized and shaped to be inserted into the through holes 204. When incorporated in a surgical instrument, the depicted articulation control 10 might be rotatable between an unarticulated position in which the external surfaces 202a block the movement of the corresponding locking members 206 and an articulated position in which the through holes 204 are aligned with the corresponding locking members 206 to permit their movement and actuation of the surgical instrument.

As noted above, in some embodiments, a portion of the handle, or the elongated shaft assembly itself, may be rotatable in order to assist in the orientation of the distal end of the elongated shaft assembly. Depending on the embodiment, it may be desirable to maintain the alignment of the articulation control and an associated locking member to ensure the proper functioning of the actuation lockout mechanism during rotation of a portion of the handle 4 or elongated shaft assembly 6. For example, in the embodiment depicted in FIGS. 4 and 5, the locking member 112 is maintained in the same orientation relative to the articulation control 10 regardless of how the handle is rotated in order to maintain the alignment of the locking member 112 with the blocking portion 10a and the non-blocking portion 10b of the articulation control. However, embodiments in which the relative orientation between the articulation control and the locking member is not maintained during rotation of a portion of the handle or elongated shaft assembly are also envisioned. For example, the articulation control could include a circumferential feature that is adapted to interact with the locking member regardless of their orientation.

As noted above, the articulation control may be adapted to articulate the articulable portion of the elongated shaft assembly between two positions, between a plurality of positions, or to any arbitrary position. Further, although the above embodiments of the articulation locking mechanism are described in reference to an unarticulated position and at least one articulated position, embodiments in which the actuation lockout is not associated with the unarticulated position are also envisioned. For example, the fastener deployment system might be prevented from actuating between two or more articulated positions. Thus, the current disclosure should not be viewed as being limited to any particular articulation position, or set of positions. In addition to the above, depending on the particular embodiment it may be desirable to selectively permit actuation of the fastener deployment system only at preselected articulation positions, or at any articulation positioning greater than a preselected threshold. In embodiments where actuation of the fastener deployment system is only permitted in one or more preselected articulated positions, the articulation control may include non-blocking portions that are only aligned with the locking member when the articulation control is positioned in one of the preselected articulated positions. For example, in one embodiment, the articulation control might be adapted to permit actuation of the fastener deployment system when it is located in one or more preselected articulation positions corresponding to articulation angles of approximately 5°, 10°, 15°, 20°, 25°, 30°, 35°, 40°, 45°, 60°, 90° or any other appropriate angle. Alternatively, in embodiments where actuation of the fastener deployment system is permitted at any articulated position greater than a preselected threshold, the articulation control may include non-blocking portions that are adapted and arranged to accommodate displacement of the locking member throughout a range of articulation positions. For example, in such an embodiment, the locking member and non-blocking portion may be aligned and actuation of the surgical instrument may be permitted when the articulation control is positioned in an articulation position corresponding to an articulation angle greater than approximately 5°, 10°, 15°, 20°, 25°, 30°, 35°, 40°, 45°, 60°, 90° or any other appropriate angle.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A method of operating a surgical instrument, the method comprising:
   moving an articulation control between a first position in which an articulable portion of an elongated shaft is arranged in a first articulation position at a first angle and a second position in which the articulable portion of the elongated shaft is arranged in a second articulation position at a second angle different from the first angle;
   receiving a locking member of a fastener deployment system in a first portion of the articulation control during actuation of the fastener deployment system when the articulation control is located in the second position; and
   blocking movement of the locking member with a second portion of the articulation control when the articulation control is in the first position.

2. The method of claim 1, wherein the articulable portion of the elongated shaft is straight relative to an elongated portion of the elongated shaft in the first articulation position.

3. The method of claim 1, wherein receiving the locking member in the first portion of the articulation control includes receiving at least one selected from the group of a rod, a crossbar, an extension, and a projection in at least one selected from the group of a through hole, a blind hole, a channel, a cutout, and a groove formed in the articulation control.

4. The method of claim 1, wherein blocking movement of the locking member comprises preventing movement of a driveshaft of the fastener deployment system.

5. The method of claim 4, wherein the driveshaft extends through a channel formed in the articulation control.

6. The method of claim 5, wherein the first portion of the articulation control is the channel.

7. The method of claim 5, wherein the first portion of the articulation control is a hole formed in the articulation control.

8. The method of claim 1, wherein moving the articulation control between the first and second positions comprises rotating the articulation control.

9. The method of claim 1, further comprising displacing the locking member into the first portion of the articulation control during actuation of the fastener deployment system.

10. A method of operating a surgical instrument, the method comprising:
    moving an articulation control between a first position in which an articulable portion of an elongated shaft is arranged in a first articulation position at a first angle and a second position in which the articulable portion of the elongated shaft is arranged in a second articulation position at a second angle different from the first angle;
    aligning a first portion of the articulation control with a locking member of a fastener deployment system when the articulation control is located in the second position, wherein the first portion is not aligned with the locking member when the articulation control is located in the first position; and
    receiving the locking member in the first portion of the articulation control when the first portion is aligned with the locking member.

11. The method of claim 10, further comprising blocking movement of the locking member with a second portion of the articulation control when the articulation control is located in the first position.

12. The method of claim 11, wherein receiving the locking member in the first portion of the articulation control includes receiving at least one selected from the group of a rod, a crossbar, an extension, and a projection in at least one selected from the group of a through hole, a blind hole, a channel, a cutout, and a groove formed in the articulation control.

13. The method of claim 11, wherein blocking movement of the locking member comprises preventing movement of a driveshaft of the fastener deployment system.

14. The method of claim 13, wherein the driveshaft extends through a channel formed in the articulation control.

15. The method of claim 14, wherein the first portion of the articulation control is the channel.

16. The method of claim 14, wherein the first portion of the articulation control is a hole formed in the articulation control.

17. The method of claim 10, wherein moving the articulation control between the first and second position comprises rotating the articulation control.

18. The method of claim 10, further comprising displacing the locking member into the first portion of the articulation control during actuation of the fastener deployment system.

19. A method of operating a surgical instrument, the method comprising:
    moving an articulation control between a first position in which an articulable portion of an elongated shaft is arranged in a first articulation position at a first angle and a second position in which the articulable portion of the elongated shaft is arranged in a second articulation position at a second angle different from the first angle;
    receiving a locking member in a first portion of the articulation control during actuation of a driveshaft operatively coupled to the locking member when the articulation control is located in the second position, and wherein the driveshaft extends through a channel formed in the articulation control.

20. The method of claim 19, further comprising blocking movement of the locking member with a second portion of the articulation control when the articulation control is in the first position to prevent movement of the driveshaft.

21. The method of claim 20, wherein receiving the locking member in the first portion of the articulation control includes receiving at least one selected from the group of a rod, a crossbar, an extension, and a projection in at least one selected from the group of a through hole, a blind hole, a channel, a cutout, and a groove formed in the articulation control.

22. The method of claim 19, wherein the first portion of the articulation control is the channel.

23. The method of claim 19, wherein the first portion of the articulation control is a hole formed in the articulation control.

24. The method of claim 19, wherein moving the articulation control between the first and second position comprises rotating the articulation control.

25. The method of claim 19, further comprising displacing the locking member into the first portion of the articulation control during actuation of the driveshaft.

* * * * *